United States Patent [19]

Schindler et al.

[11] 4,242,191

[45] Dec. 30, 1980

[54] ION SELECTIVE SENSOR AND METHOD OF MAKING SUCH SENSOR

[75] Inventors: Johannes G. Schindler, Marburg; Wilfried Schal, Bad Homburg, both of Fed. Rep. of Germany

[73] Assignee: Dr. Eduard Fresenius Chemisch-pharmazeutische Industrie KG, Apparatebau KG, Bad Homburg, Fed. Rep. of Germany

[21] Appl. No.: 37,234

[22] Filed: May 8, 1979

[30] Foreign Application Priority Data

May 10, 1978 [DE] Fed. Rep. of Germany ....... 2820475

[51] Int. Cl.³ .............................................. G01N 27/30
[52] U.S. Cl. ........................ 204/195 M; 204/195 G; 427/77
[58] Field of Search .................... 204/195 G, 195 M; 427/77

[56] References Cited

U.S. PATENT DOCUMENTS 3,479,255  11/1969  Arthur ................................ 204/1 T
3,666,651   5/1972  Makabe ............................ 204/195 G

FOREIGN PATENT DOCUMENTS 1648978  5/1972  Fed. Rep. of Germany .
2652370  5/1978  Fed. Rep. of Germany .

OTHER PUBLICATIONS

J. Montalyo, Jr. et al., Anal. Chem., vol. 41, No. 13, pp. 1897-1899, Nov. 1969.

*Primary Examiner*—G. L. Kaplan
*Attorney, Agent, or Firm*—Omri M. Behr

[57] ABSTRACT

An ion-sensitive sensor has an electron-conducting electrode and a membrane for determining the selectivity which is arranged to come into contact with a medium to be analyzed. The membrane is applied to an ion-conducting layer of glass which is in connection with the electron-conducting electrode via an ion-conductor. The membrane preferably comprises at least one organic polymer, such as PVC, having ion-active components, such as organic carrier molecules, selective ligands or ion exchangers, embedded therein. The layer of glass may also have ion-selective properties.

14 Claims, 4 Drawing Figures

ION SELECTIVE SENSOR AND METHOD OF MAKING SUCH SENSOR

BACKGROUND OF THE INVENTION

1. Field of the Invention

This invention relates to an ion-selective sensor having an electron-conducting electrode and a membrane for determining the selectivity and to a method of producing the sensor.

2. Description of the Prior Art

Ion-selective sensors serve to determine the electrochemical activity in electrolytes and can be used directly or indirectly for numerous quantitative measurements. They are therefore enjoying increasing popularity in numerous fields of physics, chemistry and medicine.

Ion-selective sensors are available in various different types of construction. The best-known is the classical construction of the glass electrode, more particularly as a pH electrode for determining hydrogen ion activity but also for measurement of other types of ions, having glass of different composition. These glass electrodes have proved to be reliable and are characterized by good stability and a long service life. One disadvantage of these electrodes lies in the fact that the properties of selectivity of the ion-selective glass available at present do not fully satisfy the user's requirements.

In latter years, specific membrane sensors have been developed in order to select particular types of ions. The contact electrode of the ligand electrolytic system is, separated from the medium to be measured or analyzed by means of a membrane made from an organic polymer. The membrane contains largely organic carrier molecules or ion-selective ligands as its effective component in a polymerized base material of the membrane. An example of an ion carrier of this type is valinomycin which has a very high selectivity for potassium ions. Very high selectivity coefficients can also be achieved by other means with certain materials. Polyvinylchloride (PVC) is often used as the base material for these membranes. In order to optimize the properties it may be necessary to introduce additionally into the membrane phase softeners for example and/or lypophilic anions.

In the case of sensors having these plastics membranes however, difficulties of a different types arise, more particularly with respect to sealing between the membrane and the sensor casing and because of the limited stability of the shape of the membrane material. The mechanical yielding thereof can for example lead to faults owing to fluctuations of the pressure in the measuring system. In the case of certain sensor constructions moreover, the permeability of the membrane to gases and water vapor may introduce measurement errors. The service life of sensors utilizing a membrane has up to now also been considerably lower than that of sensors using glass electrodes.

The present invention aims to make available an ion-selective electrode having the very high selectivity of membrane electrodes and also having a large reliability factor, a long service life and other advantageous characteristics of the glass electrode.

SUMMARY OF THE INVENTION

In accordance with the principles of the instant invention, there is provided an ion-selective electrode having an electrically conducting electrode and a membrane for determining selectivity which is arranged to come into contact with a medium to be analyzed, wherein the membrane is applied to an ion-conducting layer of glass which is in intimate contact with the electrically conducting electrode via an ion conductor.

In a preferred manner the membrane is formed directly on the layer of glass. This can be effected for example by applying a solution of the relevant plastics and of the embedded substances in a suitable solvent and by drying the same. It will be seen that the membrane bonds very well to the glass.

It is remarkable that the functioning of the electrodes in accordance with the invention is independent of the selectivity of the glass used. The selectivity characteristics of the electrode are determined exclusively by the type of ion-selective plastics layer used.

Preferably, the membrane is connected in a sealing manner to the sensor body or a special guide bushing. In accordance with one embodiment of the invention, the glass underlayer is recessed with respect to the sensor body or the guide bushing and a depression is formed which is filled with the membrane. By means of suitable selection of material it is possible for the guide bushing or the sensor body to be dissolved slightly by the solvent contained in the plastics substance so that after vaporization of the solvent an absolutely tight connection towards the outside between the plastics membrane and the guide sleeve or the bushing is achieved.

BRIEF DESCRIPTION OF THE DRAWINGS

The invention will now be further described by way of example, with reference to the drawings, in which.

DESCRIPTION OF THE PREFERRED EMBODIMENTS

Figure 1:
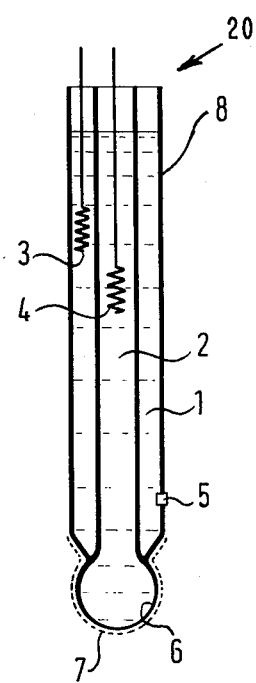
FIG. 1 shows diagrammatically one embodiment of a single rod measuring sensor, according to the principles of the present invention, in cross-section.

The single rod measuring sensor 20 shown in FIG. 1 combines an ion-selective electrode 4 and a reference electrode 3 and is constructed basically like a single rod measuring sensor made from glass of known type. The connecting head which is entirely conventional has been omitted in FIG. 1.

The electrode body 8 is manufactured from glass and contains two coaxial chambers 1 and 2 which are filled with electrolytically conducting solutions. Each chamber is provided with a conducting electrode 3, 4 which serve as a connection to a conventional current measurement circuit (not shown). The reference electrode 3 disposed in chamber 1 is connected in a known manner via a current key, which for example, may be in the form of a porous ceramic plug 5 fused into the glass wall, with the solution that is to be measured or analyzed and into which the electrode is dipped.

A spherically-shaped end element 6 of the chamber 2 comprises a thin layer of ion-conducting glass. Preferably this layer of ion-conducting glass has a thickness between 5 and $8 \times 10^{-1}$ millimeters. This glass is additionally coated with a layer 7 made from an ion-selective plastic substance. For example, an electrode of this type is preferably produced with a spherical end element 6 made from a conventional pH glass and a $Ca^{2+}$-selective coating 7. Coating takes place by applying a homogeneous mixture of the following composition.

| | |
|---|---|
| PVC in cyclohexanone (15% by weight PVC) | 10 ml |
| Calcium ion exchanger Orion No. 92-20-01/02 (Ca salt of didecylphosphoric acid in dioctylphenylphosponate). | 1.66 ml |

After vaporizing the solvent by heating to approximately 40° C. over several hours, the applied plastics layer forms an air-tight coating. Contraction of the plastics occurring during vaporization in conjunction with the spherical shaping of the electrode end element contributes to the firm bonding of the plastics layer. The electrode produced in this way exhibits a $Ca^{2+}$-selective characteristic which corresponds to the characteristics of the ion exchanger used and agrees with the characteristics of a liquid membrane electrode operating with the same ion exchanger. The selectivity is therefore exclusively determined by the outer layer coming into contact with the material under test, although the type of glass used in the example shown as a base material does have high selective characteristics per se for a different ion with a different valency. This result conforms with the third example set forth hereinafter that the selectivity characteristics of the glass are not of importance and that only the ion conductivity of the glass is important.

Figure 2:
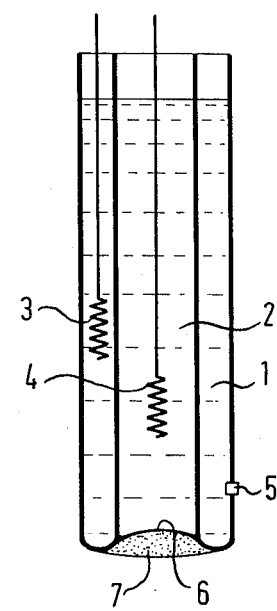
FIG. 2 shows a modification of the sensor embodiment shown in FIG. 1.

A second embodiment of the invention is shown in FIG. 2. The sensor shown in cross-section therein essentially has the same construction as in FIG. 1, but the thin layer of ion-conducting glass at the lower end of the chamber 2 is in this embodiment curved inwardly. Thus, the relatively sensitive membrane is protected with respect to mechanical effects.

Figure 3:
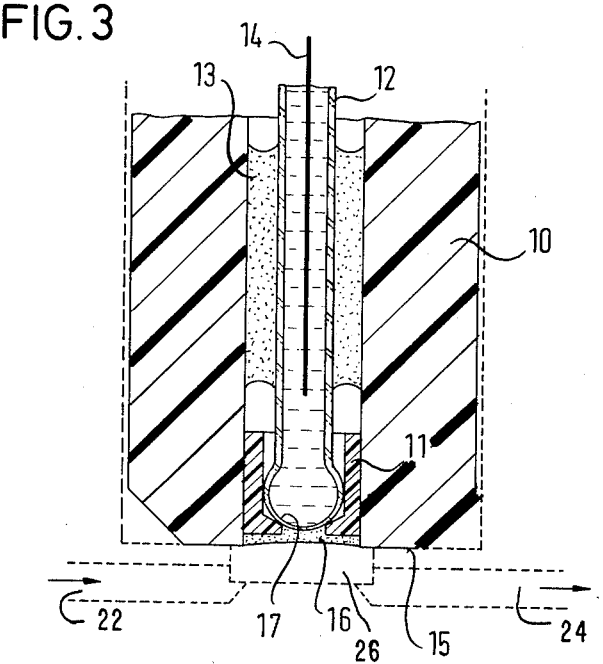
FIG. 3 shows a miniature sensor according to another embodiment of the instant invention in cross-section; and, FIG. 4 shows a simplified embodiment in cross-section of the miniature sensor shown in FIG. 3.

The embodiment shown schematically in FIG. 3 relates to a miniature electrode having an outer diameter of approximately 6 mm, preferably for insertion into an analyzer block which contains corresponding flow through channels 22 and 24 and a flow through measurement chamber 26 adjoining the endface of the electrode and indicated by the broken lines as described, for example, in German Offenlegungsschrift No. 2 652 370. The electrode body 10 has an axial borehole into the endface of which a guide bushing 11 is inserted so as to form a seal. The guide bushing accommodates the shaft and/or the spherically fused end of a glass tube 12, whereby at least this spherical and thin-walled part comprises an ion-conducting type of glass for example one of the known ion-selective glasses. The glass tube 12 is fixed moreover with the aid of a casting substance 13 in the electrode body 10. An aqueous electrolyte, for example KCl solution, is contained in the glass tube 12 into which a bypass electrode 14 is dipped, for example a chlorinated silver wire. As is known there is the possibility of solidifying the liquid electrolyte by adding suitable organic substances. Instead of the electrolytes ion-conducting solids can also be used.

The guide bushing 11 is recessed with respect to the endface 15 of the electrode body so that a flat depression is formed on the base of which (as seen from the endface of the electrode body) is located the sperical end element of the glass tube inside the borehole of the guide bushing. This depression is filled subsequently with an ion-selective plastics substance 16 which was brought into a flowable condition by means of an appropriate solvent. The material of the guide bushing 11 is selected so that it is slightly dissolved by the solvent contained in the plastics substance so that after vaporization of the solvent an absolutely sealed connection is produced. The faults (leakage potentials, "memory" effect) which are observed frequently in the case of glued or mechanically fixed membranes are avoided by this.

In an electrode constructed in accordance with FIG. 3 the spherical end element 17 of the glass tube 12 was produced for example from Na-selective glass of the type NA made by Messrs. Ingold, Frankfurt-on-Main. The ion-selective membrane 16 had the following composition taking into account the proportion of solvent (details in % by wt):

19.1%: PVC
25.0%: Cyclohexanone
55.1%: O-nitrophenyl-n-octylether (o-NPOE)
0.25%: Sodium Sodium tetraphenylborate (NA-TPB)
0.5%: Synthetic and neutral $Ca^{2+}$ carrier The synthetic neutral carrier is described in D. Ammann et al: Synthetic Neutral Carriers for Cations, in M. Kessler et al: Ion and Enzyme Electrodes in Biology and Medicine. Published by Urban & Schwarzenberg, Munich, Berlin, Vienna (1976), 22.

Acrylic glass has shown itself to be particularly suitable as a material for the guide bushing 11.

An electrode manufactured in this manner exhibits a high selectivity corresponding to the characteristics of the carrier independently of the selectivity characteristics of the end glass element 17, for $CA^{2+}$ ions and with respect to this characteristic is similar to an electrode of conventional construction manufactured by using the same carrier, however, it does have a very much longer service life.

Figure 4:
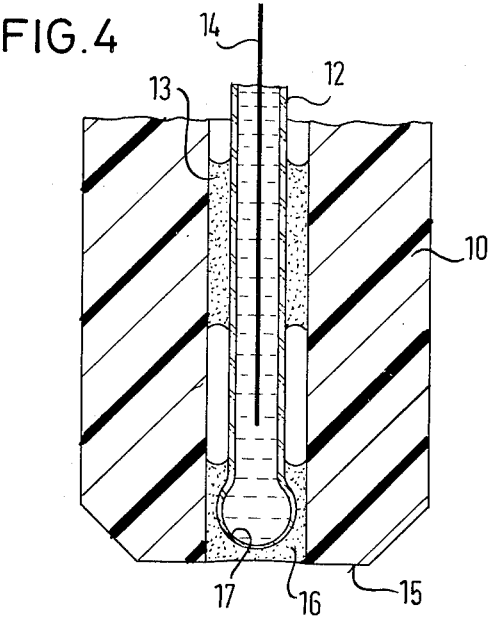

A simplified embodiment of a miniature electrode is shown in FIG. 4. The materials used are the same as in the preceding example. However, in this case, the ion-selective plastics membrane 16 encircles the entire spherical end element of the glass tube 12 and at the same time produces the seal with respect to the electrode body 10.

Not only are the already-mentioned plastics membranes with selective carrier molecules suitable as ion-selectively acting layers on an ion-conducting glass underlayer for the electrodes in accordance with the invention but also all selective membrane materials having potential-forming characteristics. Therefore not only can plastics membranes with homogeneously distributed ion-active substances be considered but so-called heterogeneous deposition membranes for example in which the most finely pulverized and difficultly soluble ion-active substances are embedded in the plastics matrix. The reference electrodes not shown in FIGS. 3 and 4 are conventional and may be placed anywhere in the flow through channel path.

Ion-selective electrodes fabricated in accordance with the principles of the instant invention can be used as sensors for direct measurement of the ion activity in a substance to be analyzed. They can also serve as a component of an indirectly-acting measuring sensor in which the ion activity is dependent on the primary reaction connected in front. An example of this is the application in enzymatic sensors in which a selective conversion of components of the medium to be analyzed takes place as a result of an enzyme arranged in known manner. Moreover the electrode described can be used as a component of a gas-sensitive measuring sensor.

We claim:

1. In an ion-selective sensor for use in a medium to be analyzed, including a first electrode having a housing with a chamber therein, said chamber bein terminated at one end by an ion-conducting layer of glass and a second electrode unit, the improvement comprising an ion-selective membrane for determining the selectivity of said electrode unit disposed upon said ion-conducting layer of glass.

2. A sensor according to claim 1, wherein said membrane comprises at least one organic polymer having ion-selectively active components embedded therein.

3. A sensor according to claim 1, wherein the ion-selectively active components comprise organic carrier molecules, selective ligands or ion exchangers.

4. A sensor according to claim 1, wherein the layer of glass also has ion-selective properties.

5. A sensor according to claim 1, further including a ligand ion conducting medium in said chamber.

6. A sensor according to claim 1, further including a solid ion conducting medium disposed in said chamber.

7. A sensor according to claim 1, wherein the membrane is disposed in a depression formed by said glass proximate one end of said first electrode.

8. A sensor according to claim 7, wherein the depression is formed by a guide bushing surrounding the ion-conducting layer of glass projecting beyond said layer of glass.

9. A sensor according to claim 8, wherein said guide bushing is made of a material which can be dissolved by said solvent.

10. A sensor according to claim 1, wherein the membrane material is soluble in an organic solvent.

11. A sensor according to claim 1, further including a hollow housing for receiving said sensor body, said membrane completely encasing the ion-conducting layer of glass and producing a seal with respect to said housing and said sensor.

12. A method of manufacturing an ion-selective sensor as described in claim 1, comprising the steps of:
(a) dissolving an organic polymer together with ion-active substances in a suitable solvent;
(b) applying said polymer to said ion-conducting layer of glass; and
(c) allowing said polymer to dry.

13. An ion-selective sensor comprising:
(a) a housing having two coaxial chambers, the inner coaxial chamber being terminated at one end in an ion-conducting layer of glass, said outer chamber adapted to communicate, via a porous medium, with a medium to be analyzed;
(b) an ion-selective membrane for determining the selectivity of said sensor coating said ion-conducting layer of glass; and
(c) first and second electrodes adapted to be connected to a measurement source, said first electrode being immersed into an ion-conducting medium disposed within said inner chamber, said second electrode being immersed into said medium to be analyzed disposed within said outer chamber.

14. In an ion-selective sensor for use in a medium to be analyzed, including the first electrode and a second electrode unit, said first electrode having a housing with a chamber therein, said chamber being terminated at one end by an ion-conducting layer of glass being coated by a membrane, the improvement wherein said membrane comprises ion-selectively active components for determining the selectivity of said sensor.

* * * * *